United States Patent
Rios Neyra et al.

(10) Patent No.: US 10,647,631 B2
(45) Date of Patent: May 12, 2020

(54) CATALYTIC PROCESS FOR DIENE DIMERIZATION

(71) Applicants: TOTAL MARKETING SERVICES, Puteaux (FR); CENTRE NATIONAL DE LA RECHERCHE SCIENTIFIQUE(CNRS), Paris (FR); UNIVERSITE CLAUDE BERNARD LYON, Villeurbanne (FR); ECOLE SUPERIEURE DE CHIMIE PHYSIQUE ELECTRONIQUE DE LYON, Villeurbanne (FR)

(72) Inventors: Cesar Rios Neyra, Villeurbanne (FR); Kai Chung Szeto, Villeurbanne (FR); Mostafa Taoufik, Villeurbanne (FR)

(73) Assignees: Total Raffinage Chimie, Courbevoie (FR); Centre National de la Recherche Scientifique (CNRS), Paris (FR); Universite Claude Bernard Lyon, Villeurbanne (FR); Ecole Superieure de Chimie Physique Electronique de Lyon, Villeurbanne (FR)

( * ) Notice: Subject to any disclaimer, the term of this patent is extended or adjusted under 35 U.S.C. 154(b) by 0 days.

(21) Appl. No.: 15/543,025

(22) PCT Filed: Jan. 11, 2016

(86) PCT No.: PCT/EP2016/050398
§ 371 (c)(1),
(2) Date: Jul. 12, 2017

(87) PCT Pub. No.: WO2016/113228
PCT Pub. Date: Jul. 21, 2016

(65) Prior Publication Data
US 2018/0002251 A1    Jan. 4, 2018

(30) Foreign Application Priority Data

Jan. 12, 2015 (EP) .................................. 15305021
Aug. 20, 2015 (EP) .................................. 15306301

(51) Int. Cl.
*C07C 2/40* (2006.01)
*C07C 5/03* (2006.01)

(52) U.S. Cl.
CPC ............... *C07C 2/403* (2013.01); *C07C 5/03* (2013.01); *C07C 2521/18* (2013.01); *C07C 2523/44* (2013.01); *C07C 2531/22* (2013.01)

(58) Field of Classification Search
CPC ....... C07C 2/403; C07C 5/03; C07C 2531/22; C07C 2523/44; C07C 2521/18
See application file for complete search history.

(56) References Cited

U.S. PATENT DOCUMENTS 3,794,692 A * 2/1974 Komatsu ................... C07C 2/04
585/508
3,801,668 A * 4/1974 Komatsu .............. B01J 31/1895
585/508

(Continued)

FOREIGN PATENT DOCUMENTS

| GB | 1061482 A | | 3/1967 | |
|---|---|---|---|---|
| GB | 1403966 | * | 8/1975 | ............. C07C 11/21 |

OTHER PUBLICATIONS

Of Marvaniya et al. ("Greener Reactions Under Solvent Free Conditions", Int. J. Drug Dev. & Res., Apr.-Jun. 2011, 3 (2): 42-51). (Year: 2011).*

*Primary Examiner* — Ali Z Fadhel
(74) *Attorney, Agent, or Firm* — Harness, Dickey & Pierce, PLC

(57) ABSTRACT

The disclosure relates to a selective head-to-head dimerization of conjugated diene compounds by a catalytic process (Continued)

in a reaction medium without solvent or with solvent comprising hydrocarbons, in the presence of a specific additive of the phenol type.

23 Claims, 2 Drawing Sheets

(56) References Cited

U.S. PATENT DOCUMENTS

| | | | | |
|---|---|---|---|---|
| 3,859,374 | A | * | 1/1975 | Komatsu ............... B01J 31/24 585/16 |
| 8,586,814 | B2 | | 11/2013 | Fisher et al. |
| 8,669,403 | B2 | | 3/2014 | Fisher et al. |
| 2009/0287032 | A1 | * | 11/2009 | Brehme ............... B01J 31/2265 585/509 |
| 2011/0287988 | A1 | * | 11/2011 | Fisher ................... C07C 2/04 508/110 |

* cited by examiner

CATALYTIC PROCESS FOR DIENE DIMERIZATION

CROSS-REFERENCE TO RELATED APPLICATIONS

This application is a National Phase Entry of International Patent Application No. PCT/EP2016/050398, filed on Jan. 11, 2016, which claims priority to European Patent Application Serial No. 15305021.6, filed on Jan. 12, 2015, and European Patent Application Serial No. 15306301.1, filed on Aug. 20, 2015 all of which are incorporated by reference herein.

TECHNICAL FIELD

The invention relates to the head-to-head dimerization of conjugated diene compounds, in particular terminal conjugated diene compounds, by a catalytic process in a reaction medium without or with solvent comprising hydrocarbons, in the presence of a specific additive, in order to provide a majority of head-to-head dimers among the reaction products.

BACKGROUND

Products obtained by dimerization of conjugated dienes and further hydrogenation may be used in different fields, such as flavors and fragrances, pharmaceutical, cosmetics, solvents and lubricants applications. in cosmetic applications, hydrogenated dimers obtained from conjugated dienes may be used in creams, such as nutrient creams and medicated creams or in toilet or milky lotion, in lipstick or in face powder. In pharmaceutical applications, hydrogenated dimers obtained from conjugated dienes may be used in medical and pharmaceutical preparations such as ointments, and medical lubricating agents. as an example of a useful hydrogenated dimer, special mention can be made to squalane, isosqualane and crocetane, obtained respectively by hydrogenation of squalene, isosqualene and crocetene.

The dimerization process of conjugated dienes is generally performed using a catalyst in the presence of a solvent. U.S. Pat. No. 8,669,403 describes the dimerization of farnesene using 2-propanol as solvent. Document WO 2011/146837 describes processes for catalytic dimerization of farnesene, said processes can be carried out in a protic solvent, such as a primary or a secondary alcohol, such as isopropanol. The protic solvents are very expensive and are thus not convenient for an industrial process. There still exists a need for the dimerization of conjugated dienes by an industrial process which would be economical and would present an improved yield and/or selectivity for the desired dimers.

Document GB 1,061,482 describes the dimerization of 1,3-butadiene in the presence of a solvent and a high amount of phenol. However, this document is silent on the issue of preparing selectively head-to-head dimers.

SUMMARY

A first object of the present invention is a process for the head-to-head dimerization of conjugated diene compounds comprising contacting, in a reaction medium, said conjugated diene compounds with a catalyst in the presence of a phenol compound. According to an embodiment of the invention, the reaction medium comprises a solvent containing hydrocarbons. According to another embodiment of the invention, the reaction medium is a medium without solvent. According to an embodiment of the invention, the conjugated diene compounds are terminal conjugated diene compounds. According to an embodiment of the invention, the conjugated diene compounds are asymmetric conjugated diene compounds.

According to an embodiment of the invention, the conjugated diene compounds have the following formula (II):

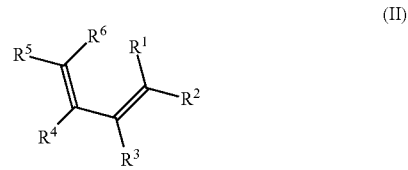

wherein $R^1$, $R^2$, $R^3$, $R^4$, $R^5$ and $R^6$ represent, independently to each other, a hydrogen atom, a halogen atom or a hydrocarbon radical, linear, branched or cyclic, saturated or unsaturated, optionally comprising one or more heteroatoms, being understood that at least one of the $R^i$ (i being 1, 2, 3, 4, 5 or 6) is different from all the others $R^i$.

According to an embodiment of the invention, the terminal conjugated diene compounds have the following formula (I):

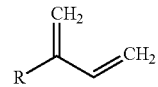

wherein R is a hydrocarbon radical having 1 to 15 carbon atoms, preferably having from 2 to 15 carbon atoms, more preferably having from 5 to 15 carbon atoms, optionally comprising one or more heteroatoms, such as nitrogen, oxygen or sulphur.

According to an embodiment, the conjugated diene compounds are selected from myrcene or farnesene. According to an embodiment, the catalyst is a homogeneous catalyst. According to another embodiment, the catalyst is a heterogeneous catalyst.

According to an embodiment of the invention, the solvent medium comprises at least 50% by weight of hydrocarbons, preferably at least 70% by weight, more preferably at least 90% by weight of hydrocarbons, still more preferably at least 99% by weight of hydrocarbons. According to an embodiment, the hydrocarbons comprised in the solvent are chosen from pentane, heptane, hexane, cyclohexane, toluene and xylene.

According to an embodiment of the invention, the phenol compound is selected from phenol, dimethylphenol, diethylphenol, mesitylphenol, 2,4,6-trimethylphenol, 2,6-di-tert-butyl-4-methylphenol, dichlorophenol, 2-hydroxybenzotrifluoride, o-methoxyphenol, diphenylphenol, o-cresol, hydroquinone, diisopropylphenol, diterbutylphenol, preferably from phenol, dimethylphenol, o-methoxyphenol, diphenylphenol, o-cresol, hydroquinone, diisopropylphenol, diterbutylphenol or 2,6-di-tertbutyl-4-methylphenol (BHT), more preferably from phenol, dimethylphenol, diisopropylphenol and diphenylphenol, even more preferably from phenol, dimethylphenol and diisopropylphenol.

According to an embodiment of the invention, the phenol compound is selected from phenol, dimethylphenol, mesitylphenol or 2,6-di-tert-butyl-4-methylphenol, preferably is phenol. According to an embodiment of the invention, the pKa of the phenol compound is of at least 9.9. According to an embodiment, the phenol compound represents from 0.2 to 8% by weight based on the total weight of the reaction medium.

According to an embodiment of the invention, the phenol compound/catalyst molar ratio is lower than or equal to 1000, preferably lower than or equal to 800, more preferably lower than or equal to 700. According to an embodiment of the invention, the catalyst is selected from palladium catalysts. According to an embodiment of the invention, the head-to-head dimer obtained represents at least 50% by weight of the reaction products, preferably at least 55% by weight of the reaction products, more preferably at least 60% by weight of the reaction products. According to an embodiment, the process of the invention further comprises a hydrogenation step, whereby hydrogenated dimers are obtained.

An advantage of the present invention is a process that involves less expensive solvents than the usual protic solvents. Another advantage of the present invention is a process leading to a satisfying yield and/or selectivity in the desired product. An advantage of the present invention is that it may be implemented without solvent, leading to a more economic process. Additionally, the absence of solvent facilitates the further separation steps, improving the efficiency of the process. An advantage of the present invention is a process that is selective, in particular, the process of the present invention leads in majority to head-to-head dimers, i.e. the head-to-head dimers represent at least 50% by weight of the reaction products, preferably at least 55% by weight, more preferably at least 60% by weight. Further features and advantages of the invention will appear from the following description of embodiments of the invention, given as non-limiting examples, with reference to the accompanying drawings listed hereunder.

DETAILED DESCRIPTION

A first object of the present invention is a process for the head-to-head dimerization of conjugated diene compounds comprising contacting, in a reaction medium, said conjugated diene compounds with a catalyst in the presence of a phenol compound.

Diene Compound

By "conjugated diene compounds" according to the present invention, it is to be understood a hydrocarbon radical, linear, branched or cyclic, comprising at least two conjugated carbon-carbon double bonds. The hydrocarbon radical may also comprise at least one heteroatom, such as oxygen, nitrogen or sulfur. Preferably, the hydrocarbon radical consists in hydrogen and carbon atoms. The hydrocarbon radical preferably comprises from 4 to 30 carbon atoms, more preferably from 5 to 20 carbon atoms. The hydrocarbon radical may optionally comprise one or more additional carbon-carbon double bonds, apart from the two conjugated carbon-carbon double bonds.

The conjugated diene compounds used in the present invention are such that the dimerization products of said conjugated diene compounds may lead simultaneously to head-to-head dimers and head-to-tail dimers (isomers). The skilled person well knows which conjugated diene compounds can form both different isomers and which conjugated diene compounds cannot form both different isomers. In particular, the conjugated diene compounds are preferably asymmetric conjugated diene compounds, such that the dimerization reaction may lead to different dimers.

Figure 2:
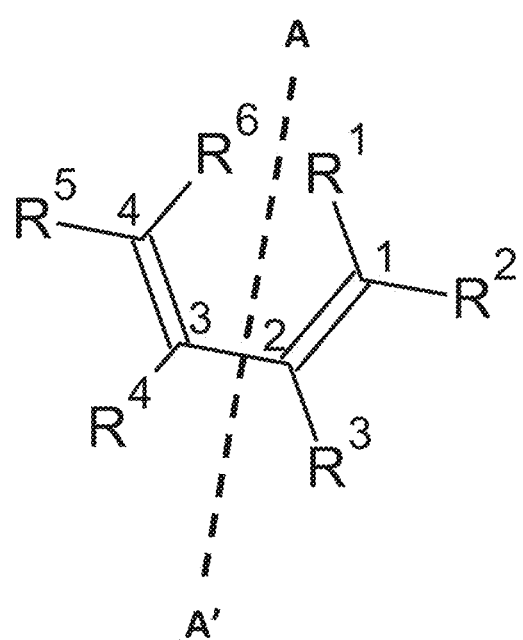
FIG. 2 represents a general formula of a conjugated diene compound.

By "asymmetric conjugated diene compound", it is to be understood a compound wherein the conjugated diene function does not comprise a plane of symmetry. The skilled person well knows what is a conjugated diene function that has a plane of symmetry or what is a conjugated diene function that has not a plane of symmetry. In this respect, and for example, 1,3-butadiene is not an assymetric conjugated diene compound. For example, with reference to the formula (II) below, an asymmetric conjugated diene compound is a compound which does not have a plane of symmetry between carbon atoms numbered 2 and 3, the plane of symmetry is represented by the AA' axis in formula (II) in FIG. 2.

A conjugated diene compound used in the present invention may be represented by the following formula (II):

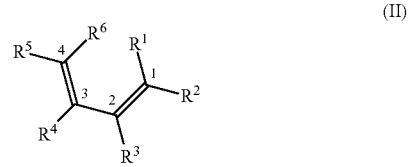

(II)

wherein $R^1$, $R^2$, $R^3$, $R^4$, $R^5$ and $R^6$ represent, independently to each other, a hydrogen atom, a halogen atom or a hydrocarbon radical, linear, branched or cyclic, saturated or unsaturated, optionally comprising one or more heteroatoms such as oxygen, nitrogen or sulphur atoms, being understood that at least one of the $R^i$ (i being 1, 2, 3, 4, 5 or 6) is different from all the others $R^i$, in order to obtain an asymmetric conjugated diene compounds.

Preferably, $R^1$, $R^2$, $R^3$, $R^4$, $R^5$ and $R^6$ represent, independently to each other, a hydrogen atom or a hydrocarbon radical having from 1 to 20 carbon atoms, preferably without heteroatoms, being understood that at least one of the $R^i$ (i being 1, 2, 3, 4, 5 or 6) is different from all the others $R^i$. According to an embodiment, $R^1$, $R^2$, $R^3$ and $R^4$ are hydrogen atoms; $R^5$ is different from $R^6$; and $R^5$ and $R^6$ are selected from a hydrogen atom or a hydrocarbon radical having from 1 to 20 carbon atoms, optionally comprising heteroatom(s). In the above formula (II) also represented in FIG. 2, the four carbon atoms of the conjugated diene function have been numbered from 1 to 4.

A "head-to-head dimer" is well known for the skilled person. For example, with reference to the formula (II) above, a head-to-head dimer is a dimer obtained by reaction between a 1-2 carbon-carbon double bond of one conjugated diene compound and the 1-2 carbon-carbon of another conjugated diene compound.

A "head-to-tail dimer" is well known for the skilled person. For example, with reference to formula (II) above, a head-to-tail dimer is a dimer obtained by reaction between a 1-2 carbon-carbon double bond of one conjugated diene compound and the 3-4 carbon-carbon double bond of another conjugated diene compound.

According to an embodiment, the conjugated diene compounds are terminal conjugated diene compounds. According to an embodiment, the terminal conjugated diene compounds have the following formula (I):

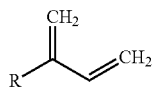

wherein R is a hydrocarbon radical, linear, branched or cyclic, saturated or unsaturated having 1 to 15 carbon atoms, optionally comprising one or more heteroatoms, such as nitrogen, oxygen or sulphur. Preferably, R is a hydrocarbon radical having from 2 to 15 carbon atoms, more preferably having from 5 to 15 carbon atoms.

According to an embodiment, the conjugated diene compounds are chosen from terpenes, such as myrcene or beta-farnesene, beta-phellandrene or alpha-terpinene, preferably from myrcene, beta-farnesene or beta-phellandrene, more preferably from myrcene or beta-farnesene. Myrcene refers to a compound having the following formula (III):

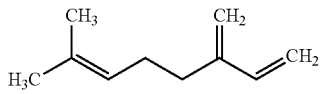

Beta-farnesene refers to a compound having the following formula (IV):

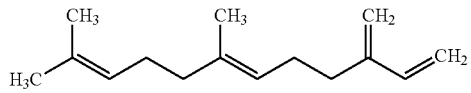

Terpenes are molecules of natural origin, produced by numerous plants, in particular conifers. By definition, terpenes (also known as isoprenoids) are a class of hydrocarbons bearing as the base unit an isoprene moiety (i.e. 2-methyl-buta-1,3-diene). Isoprene [$CH_2$=$C(CH_3)$ $CH$=$CH_2$] is represented below (V):

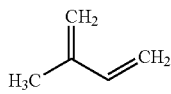

Terpenes may be classified according to the number n (integer) of isoprene units of which it is composed, for example:

n=2: monoterpenes ($C_{10}$), such as myrcene;
n=3: sesquiterpenes ($C_{15}$), such as farnesene;
n=4: diterpenes ($C_{20}$).

Alpha-terpinene is a cyclic terpene having two conjugated carbon-carbon double bonds and refers to a compound having the following formula (VI):

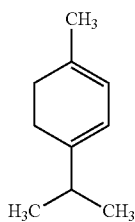

According to an embodiment, the dimerization reaction is performed with conjugated dienes of same chemical nature. According to another embodiment, the dimerization reaction is performed with conjugated dienes of different chemical natures. Preferably, the dimerization reaction is performed with conjugated dienes of same chemical nature.

The process according to the present invention may be performed in a reaction medium without solvent or with a solvent comprising hydrocarbons. Indeed, the inventors surprisingly found that the process may be performed without solvent with good results.

Solvent Medium

According to an embodiment, the dimerization process according to the invention comprises the reaction between at least two conjugated diene compounds in a solvent medium comprising hydrocarbons. These hydrocarbons are non protic compounds. They are solvents for the diene compounds. According to this embodiment of the invention, the selected hydrocarbon for the solvent medium is different from the diene compounds described above.

Preferably, the solvent medium comprises at least 50% by weight of hydrocarbons, preferably at least 70% by weight, more preferably at least 90% by weight of hydrocarbons, still more preferably at least 99% by weight of hydrocarbons, based on the total weight of the solvent medium. The hydrocarbons comprised in the solvent medium may be chosen from a linear, a branched or a cyclic hydrocarbon. For example, the hydrocarbons may be chosen from pentane, heptane, hexane, cyclohexane, toluene and xylene.

According to an embodiment of the invention, the reaction medium, wherein the dimerization reaction takes place, does not comprise protic solvents such as isopropyl alcohol. According to the meaning of the present invention, the term "solvent" preferably refers to an additional component which is different from the conjugated diene compound, different from the phenol compound additive and different from the catalyst.

Catalyst

The catalyst used in the present invention can be a homogeneous catalyst (soluble in the solvent medium) or a heterogeneous catalyst (insoluble in the solvent medium). Catalysts suitable to conduct a dimerization process are known to the one skilled in the art. For example, U.S. Pat. No. 8,669,403 and WO 2011/146837 describe some catalysts that can be used in the process of the present invention.

The catalyst may be selected from palladium catalyst or nickel catalyst, preferably from palladium catalyst. According to one embodiment, the catalyst used is a palladium catalyst. The palladium catalyst may be formed from a palladium precursor selected from [Pd(allyl)Cl]$_2$, Pd(cod)Cl$_2$, Pd2(dba)$_3$, Pd(dba)$_2$, Pd(dba), Pd(acac)$_2$, or an equimolar mixture of Pd(dba)$_3$ and Pd$_2$(dba)$_3$. The catalyst may further comprise a ligand selected from triphenyl phosphine, triethyl phosphine and tritolyl phosphine, preferably from triphenyl phosphine.

Phenol Compound

The process of dimerization according to the present invention is performed in the presence of a phenol compound. By "phenol compound" according to the present invention, it is to be understood a compound comprising at least one group of formula:

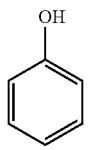

According to the present invention, the phenol compound is selected from phenol or phenol-containing compounds. The phenol-containing compound (also named sterically hindered phenol) is a phenol substituted by one or more substituents. The substituents may be chosen from methyl, ethyl, propyl, tertiobutyl or mesityl groups, for example from methyl, ethyl or propyl groups. Preferably, the phenol-containing compound is substituted in ortho position of the OH function of the phenol by one or two substituents.

According to an embodiment of the invention, the phenol compound is selected from phenol, dimethylphenol, diethylphenol, mesitylphenol, 2,4,6-trimethylphenol, 2,6-di-tert-butyl-4-methylphenol, dichlorophenol, 2-hydroxybenzotrifluoride, o-methoxyphenol, diphenylphenol, o-cresol, hydroquinone, diisopropylphenol, diterbutylphenol, preferably from phenol, dimethylphenol, o-methoxyphenol, diphenylphenol, o-cresol, hydroquinone, diisopropylphenol, diterbutylphenol or 2,6-di-tertbutyl-4-methylphenol (BHT), more preferably from phenol, dimethylphenol, diisopropylphenol and diphenylphenol, even more preferably from phenol, dimethylphenol and diisopropylphenol. According to an embodiment of the invention, the phenol compound is selected from dimethylphenol, diisopropylphenol and diphenylphenol, preferably from dimethylphenol and diisopropylphenol. According to an embodiment of the invention, the phenol compound is selected from phenol, dimethylphenol, mesitylphenol or 2,6-di-tert-butyl-4-methylphenol.

The inventors surprisingly found that the addition of a phenol compound in the reaction medium improved the yield and/or the selectivity of the dimerization reaction in case a conventional and less expensive solvent is used, such as an hydrocarbon. The inventors also surprisingly found that the addition of a phenol compound in the reaction medium improved the yield and/or selectivity of the dimerization reaction even in a reaction medium which does not comprise any solvent.

Preferably, the phenol compound is a phenol, i.e. a non-substituted phenol. According to an embodiment, the phenol compound represents, by weight, from 0.2 to 2%, preferably from 0.4 to 1%, ideally around 0.6%, of the reaction medium (solvent+diene+phenol). Alternatively, the phenol compound/diene compound weight ratio at the beginning of the reaction may range from 0.2 to 9.0, preferably from 1.0 to 6.0.

According to an embodiment of the invention, the pKa of the phenol compound is preferably higher than or equal to 9.9. It has been observed, in particular with homogeneous catalysis, that if the pKa of the phenol compound is higher than or equal to 9.9, then the conversion may be improved and the selectivity towards the head-to-head dimer may also be improved. According to an embodiment of the invention, the pKa of the phenol compound may be less than or equal to 12.

Reaction Process

The reaction is preferably performed at a temperature comprised between 25° C. and 150° C., preferably between 25° C. and 120° C., more preferably from 50° C. to 120° C. At higher temperatures, there is a risk that the diene polymerizes, according to a Diels-Alder reaction leading to an undesired cyclic dimer. For example, the temperature may range from 50° C. to 95° C.

The reaction is preferably performed in an inert gas atmosphere, for example in argon or nitrogen atmosphere, preferably at atmospheric pressure. The reaction is preferably performed during at least 5 hours, preferably at least 8 hours, more preferably during from 8 to 36 hours, ideally from 12 to 24 hours.

The reaction is preferably performed with a molar ratio conjugated dienes/catalyst ranging from 200 to 5000, preferably from 500 to 3000, more preferably from 1000 to 2000. Alternatively, the reaction may be performed with a conjugated diene compounds/catalyst molar ratio ranging from 1000 to 30000, preferably from 2000 to 25000, more preferably from 5000 to 20000. The reaction is preferably performed with a molar ratio phenol compound/catalyst ranging from 10 to 200, preferably from 20 to 100. Alternatively, the reaction may be performed with a molar ratio phenol compound/catalyst ranging from 10 to 3200, preferably from 60 to 640.

According to an embodiment, the phenol compound/catalyst molar ratio at the beginning of the dimerization reaction is lower than or equal to 1000, preferably lower than or equal to 800, more preferably lower than or equal to 700. According to an embodiment of the invention, the phenol compound/catalyst molar ratio at the beginning of the dimerization reaction ranges from 10 to 1000, preferably from 30 to 800, more preferably from 50 to 700. According to an embodiment of the invention, when the molar ratio phenol compound/catalyst is less than or equal to 200, preferably less than or equal to 100, then the molar ratio conjugated dienes/catalyst is preferably less than or equal to 8000, preferably less than or equal to 6000.

The reaction can be a batch reaction, a semi-batch reaction or a continuous reaction and preferably takes place in a stirred reactor. Upon completion of the reaction, which under the said process conditions yields a high selectivity and a high conversion, the resulting dimerization product can be separated off from the reactor stream in a manner known per se, for instance by distillation, absorption, etc.

The dimerization product can further be submitted to a hydrogenation reaction in the presence of a hydrogenation catalyst. The step of hydrogenation may be carried out by methods well known for the skilled person. For example, the step of hydrogenation may be performed with hydrogen in the presence of a hydrogenation catalyst, such as Pd/C, Raney nickel or Ni/Al$_2$O$_3$.

After hydrogenation, hydrogenated dimers are obtained, such as crocetane, squalane or isosqualane, hydrogenated dimer of alpha-terpinene, hydrogenated dimer of beta-phellandrene. Preferably, dimers obtained after the hydrogenation are saturated dimers.

The process of the invention leads to reaction products containing the desired head-to-head dimers. However, a dimerization reaction of conjugated diene compounds may lead to different reaction products. The reaction products may be dimers, trimers, etc. . . . . . Different dimers may be obtained, such as head-to-head dimers or head-to-tail dimers (isomers).

The process according to the present invention allows improving the selectivity of the process. In particular, the use of the combination of the hydrocarbon-containing solvent medium and the phenol compound allows improving the selectivity for the head-to-head dimer. The "selectivity for compound X" refers to the amount of compound X formed in the dimerization reaction based on the total amount of products formed. The selectivity is expressed as a percentage by weight. Preferably, the head-to-head dimer obtained represents at least 50% by weight of the reaction products, preferably at least 55% by weight of the reaction products, more preferably at least 60% by weight of the reaction products.

EXAMPLES

Examples 1 to 3

Figure 1:
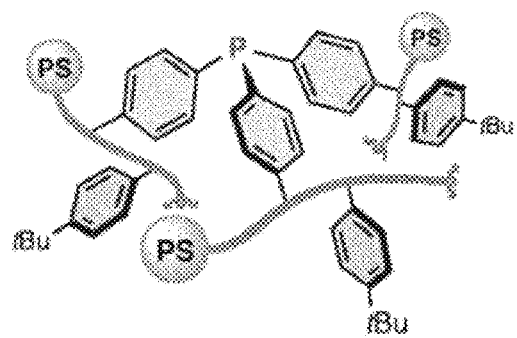
FIG. 1 represents a polystyrene-triphenylphosphane hybrid polymer.

Examples have been performed using myrcene as conjugated diene, and a Pd based heterogeneous catalyst (polystyrene-triphenylphosphane hybrid polymer, such as described in FIG. 1):

Example 1: reaction with heptane as solvent and phenol as additive

Example 2: reaction with isopropanol as solvent and phenol as additive

Example 3: reaction with isopropanol as solvent without phenol.

For examples 1 and 2, the protocol was as follows:

The phosphine hybrid polymer (0.200 g, 0.018 mmol, 1 eq), Palladium(II) acetylacetonate catalyst (5.5 mg, 0.018 mmol, 1 eq.), Myrcene (molar ratio myrcene/catalyst=2000, 4.9 g, 36 mmol) and Phenol (0.101 g, 1.08 mmol, 60 eq.) were charged in a 100 mL schlenk. Then, 15 mL of solvent (isopropanol or heptane) was added under atmospheric pressure of Argon or nitrogen to this mixture and stirred for 12 h at 100° C. Finally, the crude of the dimerization reaction was filtrated through a silica path on Büchner fritted disc funnel and washed several times with toluene. The solvent was evaporated in the rotavapor. The crude (0.160 g) was then hydrogenated in an auto-clave (100 mL) with 7 mL of Toluene, 0.150 g of Pd/C (10 wt % load), 40 bar of hydrogen at 85° C. for 12 h. Finally, an aliquot of the product with an internal standard dodecane was injected in GC-FID. The results are presented in the table 1.

For example 3, the protocol was as follows: The phosphine hybrid polymer (0.200 g, 0.018 mmol, 1 eq), Palladium(II) acetylacetonate catalyst (5.5 mg, 0.018 mmol, 1 eq), Myrcene (molar ratio myrcene/catalyst=500, 1.2 g, 9 mmol) were charged in a 100 mL schlenk. Then, 15 mL of isopropanol was added under atmospheric pressure of Argon or nitrogen to this mixture and stirred for 12 h at 100° C. Finally, the crude of the dimerization reaction was filtrated through a silica path on Büchner fritted disc funnel and washed several times with toluene. The solvent was evaporated in the rotavapor. The crude (0.160 g) was then hydrogenated in an auto-clave (100 mL) with 7 mL of Toluene, 0.150 g of Pd/C (10 wt % load), 40 bar of hydrogen at 85° C. for 12 h. Finally, an aliquot of the product with an internal standard dodecane was injected in GC-FID. The results are presented in the table 2.

Conditions for the Hydrogenation—for the Analysis of the Dimerization Products

The crude of the dimerization reaction (0.089 g) was charged in a stainless steel autoclave with 10 wt % Pd/C (150 mg), 5 mL of toluene, 40 bar of $H_2$ and stirred for 12 h at 85° C. After that, an internal standard nonadecane (80 mg) was added to the hydrogenated mixture and an aliquot was injected in the GC-FID to obtain the conversion and selectivity on dimers. The conversion was mainly calculated based on the latter method unless further specification. The diene conversion refers to the amount in percentage by weight of diene that has reacted.

The chemical reactions involved in the examples 1 to 3 are the following:

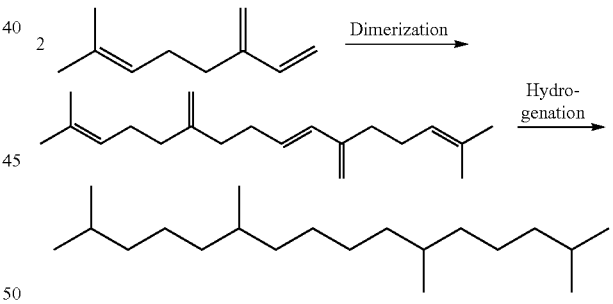

The conversion and the selectivity obtained in the examples are indicated in the two tables below.

TABLE 1 conversion and selectivity of examples 1 and 2

|  | Myrcene conversion (%) | Head-to-head dimer | Selectivity (%) | | | | Molar ratio (head-to-head dimer/head-to-tail dimer) |
|---|---|---|---|---|---|---|---|
|  |  |  | Other dimers | Trimers | Phenoxy-dimer | Head-to-tail dimer |  |
| Ex. 1 | 68 | 77.7 | 4.9 | 4.1 | 4.3 | 9.0 | 8.6 |
| Ex. 2 | 90 | 60.8 | 18.9 | 15.8 | — | 4.5 | 13.4 |

TABLE 2 conversion and selectivity of example 3

| | Myrcene conversion (%) | Selectivity (%) | | | | Molar ratio (head-to-head dimer/head-to-tail dimer) |
| --- | --- | --- | --- | --- | --- | --- |
| | | Head-to-head dimer (crocetane) | Other dimers | Trimers | Head-to-tail dimer | |
| Example 3 | 88 | 65.5 | 9.1 | 21.7 | 3.7 | 17.7 |

Example 1 according to the present invention shows that the addition of an additive such as phenol in a hydrocarbon solvent such as heptane improves the head-to-head dimer selectivity. On the contrary, example 2 shows that the addition of phenol in a protic solvent such as isopropanol gives a head-to-head dimer selectivity that is less than the head-to-head selectivity of example 1.

The inventors have noted that the conversion can be increased by increasing the amount of phenol. The inventors have also found that the selectivity for phenoxy-dimers decreases if the reaction time is increased.

Examples 4 to 7

Examples have been performed using myrcene as conjugated diene compound, and a homogeneous palladium catalyst Pd(acac)$_2$PPh$_3$. The same dimerization reaction followed by hydrogenation reaction as in examples 1 to 3 is obtained.

The experimental conditions of each example 4 to 7 are indicated in the table 3 below.

TABLE 3 experimental conditions of examples 4 to 7

| | Solvent volume (mL) | myrcene/Pd molar ratio | Phenol volume (mL) |
| --- | --- | --- | --- |
| Ex. 4 | 0 | 10000 | 1 |
| Ex. 5 | 0 | 20000 | 1 |
| Ex. 6 | 5 | 10000 | 1 |
| Ex. 7 | 10 | 10000 | 1 |

Palladium(II) acetylacetonate catalyst (5.5 mg, 0.018 mmol, 1 eq), triphenylphosphine ligand (4.7 mg, 0.018 mmol, 1 eq), and Phenol (1 mL, 11.52 mmol, 640 eq) and optionally solvent (heptane) were charged in a 100 mL schlenk. After 20 min agitation, Myrcene (molar ratio myrcene/catalyst=10000, 24.5 g, 180 mmol) is added via a syringe. The mixture is stirred at atmospheric pressure under a low flow of argon or nitrogen for 12 h at 115° C. In absence of solvent, myrcene is directly added to the Schlenk at the same time as the other reactants. Finally, the crude of the dimerization reaction was filtrated through a silica path on Büchner fritted disc funnel and washed several times with toluene. The solvent was evaporated in the rotavapor. The crude (0.160 g) was then hydrogenated in an auto-clave (100 mL) with 7 mL of Toluene, 0.150 g of Pd/C (10 wt % load), 40 bar of hydrogen at 85° C. for 12 h. Finally, an aliquot of the product with an internal standard dodecane was injected in GC-FID which results are presented in the table 4.

The conversion and the selectivity obtained in the examples are indicated in the table 4 below.

TABLE 4 conversion and selectivity

| | Conversion (%) | Selectivity (%) | | | | |
| --- | --- | --- | --- | --- | --- | --- |
| | | Head-to-head dimer | other | Trimer | Phenoxy dimer | Head-to-tail dimer |
| Ex. 4 | 92 | 67.2 | 7.7 | 4.3 | 3 | 17.8 |
| Ex. 5 | 86 | 69.4 | 10.6 | 4.7 | 3 | 12.3 |
| Ex. 6 | 91 | 67.1 | 6.8 | 4.4 | 2.4 | 19.3 |
| Ex. 7 | 92 | 64.3 | 10.1 | 4.8 | 3.4 | 17.4 |

As illustrated in the table 4, the examples 4 and 5 without solvent allows providing similar conversion as examples 6 and 7 with solvent. We can also note, that for all examples 4 to 7 the head-to-head dimer is mainly obtained, in particular the selectivity towards the head-to-head dimer is more than 60% for each example 4 to 7. Examples 8 to 44 as detailed below have been performed using farnesene as conjugated diene compound (instead of myrcene).

The head-to-head dimer obtained after hydrogenation is the squalane which can be represented by the following formula:

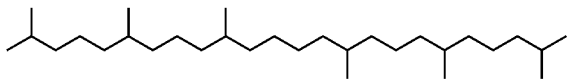 [SMILES: CC(C)CCCC(C)CCCC(C)CCCCC(C)CCCC(C)CCCC(C)C]

Examples 8 to 11

Effect of the addition of phenol in a process implemented in a solvent containing hydrocarbons (heptane) or without solvent. For all the examples 8-11, a similar protocol as the protocol of example 4 was used with the following conditions:

the temperature is 115° C.;

the reaction time is 12 h;

the catalyst is a homogeneous catalyst: Pd(Acac)$_2$PPh$_3$.

Other conditions are indicated in table 5 below.

TABLE 5 experimental conditions of examples 8-11

| | solvent | Molar ratio phenol compound/Pd (phenol compound) | Temperature (° C.) | Molar ratio Farnesene/Pd |
| --- | --- | --- | --- | --- |
| Ex. 8 | Heptane 15 mL | 0 | 100 | 500 |
| Ex. 9 | Heptane 15 mL | 60 (phenol) | 100 | 500 |
| Ex. 10 | No solvent | 0 | 115 | 10000 |
| Ex. 11 | No solvent | 630 (phenol) | 115 | 10000 |

Conversions and selectivities are indicated in table 6 below.

TABLE 6 conversion and selectivity of examples 8 and 9

|  | Farnesene conversion (%) | Head-to-head dimer (squalane) | Others | Trimers | Head-to-tail dimer (isoqualane) |
|---|---|---|---|---|---|
| Ex. 8 | 7 | — | — | — | — |
| Ex. 9 | 82 | 76 | — | — | 7 |
| Ex. 10 | 30 | 32.4 | 62.2 | 1.5 | 3.9 |
| Ex. 11 | 97 | 77.2 | 4.8 | 4.7 | 13.3 |

Selectivity (% by weight)

As can be seen in table 6, the process performed in a solvent comprising hydrocarbons without phenol as additive (Ex. 8) does not provide a satisfying conversion (only 7% of conversion). On the contrary, the process performed in a solvent comprising hydrocarbons with phenol as additive (Ex. 9) provides a satisfying conversion (82%) with a satisfying selectivity towards the head-to-head dimer (76%).

We can also see that the process performed without solvent and without phenol compound as additive (Example 10) does not provide a satisfying conversion (only 30% of conversion) and the selectivity towards the head-to-head dimer is not satisfying (squalane represents only 32.4% by weight of the reaction products). On the contrary, a similar process performed without solvent and with phenol as additive provides a conversion of 97% with a good selectivity towards the head-to-head dimer (77.2% by weight).

Examples 12 to 19

Process according to the invention implemented with several solvent conditions. For all the examples 12 to 19, a similar protocol as the protocol of example 4 was used with the following conditions:
  the molar ratio phenol compound/Pd, the phenol compound being phenol, is 640;
  the reaction time is 12 h;
  the temperature is 115° C.;
  the catalyst is a homogeneous catalyst: $Pd(Acac)_2PPh_3$.
Other conditions are indicated in table 7 below.

TABLE 7 experimental conditions and conversion of examples 12-19

|  | Solvent (amount) | Molar ratio Farnesene/Pd | Conversion (% by weight) |
|---|---|---|---|
| Ex. 12 | No solvent | 10000 | 97 |
| Ex. 13 | No solvent | 20000 | 96 |
| Ex. 14 | Cyclohexane (21 mL) | 10000 | 93.7 |
| Ex. 15 | Cyclohexane (10 mL) | 10000 | 97 |
| Ex. 16 | Cyclohexane (5 mL) | 10000 | 97 |
| Ex. 17 | Heptane (21 mL) | 10000 | 96 |
| Ex. 18 | Heptane (10 mL) | 10000 | 97 |
| Ex. 19 | Heptane (5 mL) | 10000 | 97 |

As can be seen in table 7 above, with or without solvent, the conversion is very satisfying. Furthermore, we can see that for different kinds of solvents and different amounts of solvent, the conversion is satisfying.

The selectivity is indicated in table 8 below.

TABLE 8 selectivity

| | Head-to-head dimer (squalane) | others | Trimers | Phenoxy squalane | Head-to-tail dimer (isoqualane) |
|---|---|---|---|---|---|
| Ex. 12 | 77.2 | 4.8 | 4.7 | 0 | 13.3 |
| Ex. 13 | 78.2 | 10.4 | 3.6 | 0.4 | 7.4 |
| Ex. 14 | 76.7 | 3.7 | 2.4 | 4.7 | 12.5 |
| Ex. 15 | 78.1 | 4.4 | 4 | 0.3 | 13.2 |
| Ex. 16 | 76.4 | 4.6 | 6.4 | 0.3 | 12.3 |
| Ex. 17 | 79.9 | 3.2 | 4.6 | 0.3 | 12 |
| Ex. 18 | 72.2 | 4.4 | 5.9 | 5.5 | 12 |
| Ex. 19 | 73.6 | 5.1 | 1.2 | 7.7 | 12.4 |

Selectivity (% by weight)

As can be seen in table 8, the selectivity towards the head-to-head dimer is very satisfying, since squalane represents more than 70% by weight of the reaction products for all the examples.

Examples 20 to 23

Effect of the molar ratio conjugated diene compound/catalyst. The same protocol as the protocol used in example 4 has been implemented for examples 20 to 23 with the following parameters:
  No solvent;
  the molar ratio phenol compound/Pd, the phenol compound being phenol, is 60;
  the temperature is 115° C.;
  the reaction time is 12 h;
  the catalyst is a homogeneous catalyst: $Pd(Acac)_2PPh_3$.

TABLE 9 experimental conditions and conversion of examples 20-23

|  | Molar ratio Farnesene/Pd | Conversion (% by weight) |
|---|---|---|
| Ex. 20 | 1000 | 97 |
| Ex. 21 | 2000 | 97 |
| Ex. 22 | 3000 | 97 |
| Ex. 23 | 6000 | 75 |

The selectivity for examples 20-23 is indicated in table 10 below.

TABLE 10 selectivity

|  | Head-to-head dimer (squalane) | others | Trimers | Head-to-tail dimer (isoqualane) |
|---|---|---|---|---|
| Ex. 20 | 83.1 | 4.7 | 1.3 | 10.8 |
| Ex. 21 | 83.1 | 6.9 | 3.4 | 6.6 |
| Ex. 22 | 81 | 9.9 | 2.9 | 6.1 |
| Ex. 23 | 71.1 | 21.2 | 1.5 | 6.2 |

Selectivity (% by weight)

As illustrated in tables 9 and 10, we can see that the process of the invention provides satisfying conversions with a good selectivity for the head-to-head dimer.

Examples 24-34 effect of the nature of the phenol compound. The same protocol as the protocol used in example 4 has been implemented for examples 24 to 34 with the following parameters:

No solvent;
the temperature is 115° C.;
the reaction time is 12 h;
the molar ratio phenol compound/Pd is 60;
the catalyst is a homogeneous catalyst: Pd(Acac)$_2$PPh$_3$.

The formula of the phenol compounds that have been tested is represented below for each compounds:

phenol:

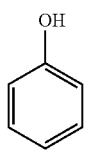

dimethylphenol:

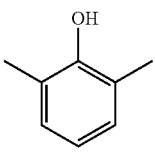

2-hydroxybenzotrifluoride:

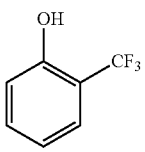

o-methoxyphenol:

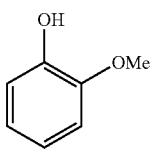

diphenylphenol:

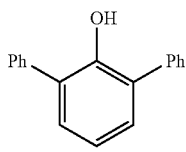

o-cresol:

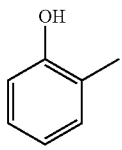

hydroquinone:

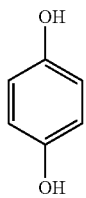

diisopropylphenol:

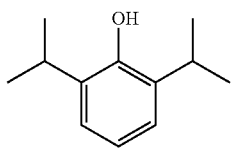

ditertbutylphenol:

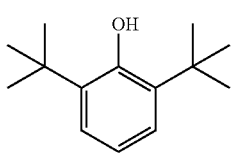

ditertbutylmethylphenol (BHT):

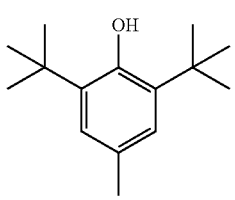

Other conditions are indicated in table 11 below.

TABLE 11 experimental conditions and conversion of examples 24-34

| | Phenol compound | pKa of the phenol compound | Molar ratio Farnesene/ Pd | Conversion (% by weight) |
|---|---|---|---|---|
| Ex. 24 | Phenol | 9.9 | 3000 | 97 |
| Ex. 25 | dimethylphenol | 11 | 3000 | 96 |
| Ex. 26 | 2-hydroxybenzotrifluoride | 8.12 | 3000 | 85 |
| Ex. 27 | o-methoxyphenol | 9.98 | 3000 | 96 |
| Ex. 28 | Diphenylphenol | 10.02 | 3000 | 98 |
| Ex. 29 | o-cresol | 10.28 | 3000 | 96 |
| Ex. 30 | Hydroquinone | 10.33 | 3000 | 95 |
| Ex. 31 | Diisopropylphenol | 11 | 3000 | 96.9 |
| Ex. 32 | Ditertbutylphenol | 12.16 | 3000 | 82.4 |
| Ex. 33 | Ditertbutylmethylphenol (BHT) | 12.76 | 3000 | 85.6 |
| Ex. 34 | Diisopropylphenol | 11 | 5000 | 80 |

The selectivity for examples 24-34 is indicated in table 12 below.

TABLE 12 selectivity

| | Selectivity (% by weight) | | | |
|---|---|---|---|---|
| | Head-to-head dimer (squalane) | others | Trimers | Head-to-tail dimer (isoqualane) |
| Ex. 24 | 81 | 9.9 | 2.9 | 6.1 |
| Ex. 25 | 84.6 | 6.1 | 3.2 | 5.8 |
| Ex. 26 | 74 | 11.2 | 4 | 10.8 |
| Ex. 27 | 81 | 10.4 | 3 | 5.6 |
| Ex. 28 | 86.3 | 4.3 | 2.2 | 7.2 |
| Ex. 29 | 81 | 10.8 | 2.1 | 6.1 |
| Ex. 30 | 81.7 | 8.7 | 3.4 | 6.2 |
| Ex. 31 | 87.8 | 4.5 | 2.2 | 5.5 |
| Ex. 32 | 68.8 | 23.4 | 1.9 | 5.9 |
| Ex. 33 | 70.3 | 21.7 | 1.7 | 6.3 |
| Ex. 34 | 80.6 | 11.4 | 2.7 | 5.3 |

As illustrated in tables 11 and 12, we can see that the process of the invention provides satisfying conversions with a good selectivity for the head-to-head dimer for different phenol compounds used as additive during the process.

Examples 35-38

Effect of the amount of phenol compound. The same protocol as the protocol used in example 4 has been implemented for examples 35 to 38 with the following parameters:
No solvent;
the temperature is 115° C.;
the reaction time is 12 h;
the catalyst is a homogeneous catalyst: Pd(Acac)$_2$PPh$_3$.
Other conditions are indicated in table 13 below.

TABLE 13 experimental conditions and conversion of examples 35-38

|  | Phenol compound | Molar ratio phenol compound/Pd | Molar ratio Farnesene/Pd | Conversion (% by weight) |
|---|---|---|---|---|
| Ex. 35 | Phenol | 640 | 10000 | 97 |
| Ex. 36 | Phenol | 320 | 10000 | 93 |
| Ex. 37 | Diisopropylphenol | 30 | 3000 | 92.4 |
| Ex. 38 | diisopropylphenol | 320 | 3000 | 96 |

The selectivity for examples 35-38 is indicated in table 14 below.

TABLE 14 selectivity

| | Selectivity (% by weight) | | | |
|---|---|---|---|---|
|  | Head-to-head dimer (squalane) | others | Trimers | Head-to-tail dimer (isoqualane) |
| Ex. 35 | 77.2 | 4.8 | 4.7 | 13.3 |
| Ex. 36 | 79.4 | 11.3 | 1.3 | 7.9 |
| Ex. 37 | 81.3 | 10.9 | 2.3 | 5.5 |
| Ex. 38 | 86.4 | 4.9 | 2.9 | 5.8 |

We can see that the process of examples 35-38 according to the present invention provides a good conversion and a good selectivity regarding the head-to-head dimer, since squalane represents more than 75% by weight of the reaction products.

Example 39

Process of the invention implemented at a higher temperature. The same protocol as the protocol used in example 4 has been implemented for example 39 with the following parameters:
no solvent;
the molar ratio phenol compound/Pd, the phenol compound being phenol, is 320;
the temperature is 130° C.;
the reaction time is 12 h;
the catalyst is a homogeneous catalyst: Pd(Acac)$_2$PPh$_3$;
the molar ratio farnesene/Pd is 10000.

The results for example 39 are the following:
conversion: 96% by weight;
Selectivity:
head-to-head dimer (squalane): 78.7% by weight;
others: 9.2% by weight;
trimers: 4.7% by weight;
head-to-tail dimer (isosqualane): 7.3% by weight.
Thus, we can see that at 130° C., the process of the invention provides a satisfying conversion with a good selectivity regarding the head-to-head dimer.

Examples 40 to 44

Process according to the invention using a heterogeneous catalyst. The same protocol as the protocol used in example 1 has been implemented for examples 40-44 with the following parameters:
the temperature is 115° C.;
the reaction time is 12 h;
the catalyst is a heterogeneous catalyst: palladium phosphine hybrid polymer (such as described in FIG. 1).
Other conditions are indicated in table 15 below.

TABLE 15 experimental conditions and conversion of examples 40-44

|  | Phenol compound | Molar ratio phenol compound/Pd | Molar ratio Farnesene/Pd | Conversion (% by weight) |
|---|---|---|---|---|
| Ex. 40 | Phenol | 640 | 10000 | 89.3 |
| Ex. 41 | Phenol | 640 | 10000 | 93 |
| Ex. 42 | Phenol | 60 | 3000 | 96 |
| Ex. 43 | Dimethylphenol | 60 | 3000 | 96 |
| Ex. 44 | diisopropylphenol | 60 | 3000 | 95 |

The selectivity is indicated in table 16 below.

TABLE 16 selectivity

| | Selectivity (% by weight) | | | | |
|---|---|---|---|---|---|
|  | Head-to-head dimer (squalane) | others | Trimers | Phenoxy squalane | Head-to-tail dimer (isoqualane) |
| Ex. 40 | 62.2 | 8.8 | 9.4 | 3.9 | 15.7 |
| Ex. 41 | 63 | 15.7 | 4.6 | 0 | 16.7 |
| Ex. 42 | 80.4 | 9.3 | 3.6 | 0 | 6.7 |
| Ex. 43 | 79.6 | 10.8 | 3.9 | 0 | 5.7 |
| Ex. 44 | 72.3 | 18.1 | 4.3 | 0 | 5.3 |

We observe that the process of the invention can be performed using a heterogeneous catalyst and provide a good conversion (more than 89% by weight) and can provide satisfying selectivity regarding the head-to-head dimer since squalane represents more than 60% by weight of the reaction products, whereas the head-to-tail dimer represents less than 17% by weight of the reaction products.

The invention claimed is:
1. A process for the head-to-head dimerization of farnesene, the process comprising contacting the farnesene with a catalyst in the presence of a phenol compound and in the absence of a solvent, wherein said catalyst comprises a ligand selected from triphenyl phosphine, triethyl phosphine and tritolyl phosphine.
2. The process according to claim 1, wherein the farnesene is beta-farnesene.

3. The process according to claim 1, wherein the catalyst is a homogeneous catalyst.

4. The process according to claim 1, wherein the catalyst is a heterogeneous catalyst.

5. The process according to claim 1, wherein the phenol compound is selected from phenol, dimethylphenol, diethylphenol, mesitylphenol, 2,4,6-trimethylphenol, 2,6-di-tert-butyl-4-methylphenol, dichlorophenol, 2-hydroxybenzotrifluoride, o-methoxyphenol, diphenylphenol, o-cresol, hydroquinone, diisopropylphenol, or diterbutylphenol.

6. The process according to claim 1, wherein the phenol compound is selected from phenol, dimethylphenol, mesitylphenol or 2,6-di-tert-butyl-4-methylphenol.

7. The process according to claim 1, wherein the pKa of the phenol compound is higher than or equal to 9.9.

8. The process according to claim 1, wherein the phenol compound represents from 0.2 to 8% by weight based on the total weight of the reaction medium.

9. The process according to claim 1, wherein the phenol compound/catalyst molar ratio is lower than or equal to 1000.

10. The process according to claim 1, wherein the catalyst is selected from palladium catalysts.

11. The process according to claim 1, wherein the head-to-head dimer obtained represents at least 50% by weight of the reaction products.

12. The process according claim 1, further comprising a hydrogenation step to obtain hydrogenated dimers.

13. The process according to claim 1, wherein said catalyst is formed from a palladium precursor selected from [Pd(allyl)Cl]$_2$, Pd(cod)Cl$_2$, Pd$_2$(dba)$_3$, Pd(dba)$_2$, Pd(dba), Pd(acac)$_2$, or an equimolar mixture of Pd(dba)$_3$ and Pd$_2$(dba)$_3$.

14. A process for the head-to-head dimerization of myrcene, the process comprising contacting myrcene with a catalyst in the presence of a phenol compound and in the absence of solvent; wherein said catalyst comprises a ligand selected from the group consisting of triphenyl phosphine, triethyl phosphine and tritolyl phosphine.

15. The process according to claim 14, wherein the phenol compound is selected from phenol, dimethylphenol, diethylphenol, mesitylphenol, 2,4,6-trimethylphenol, 2,6-di-tert-butyl-4-methylphenol, dichlorophenol, 2-hydroxybenzotrifluoride, o-methoxyphenol, diphenylphenol, o-cresol, hydroquinone, diisopropylphenol, or diterbutylphenol.

16. The process according to claim 14, wherein the phenol compound is selected from phenol, dimethylphenol, mesitylphenol or 2,6-di-tert-butyl-4-methylphenol.

17. The process according to claim 14, wherein the pKa of the phenol compound is higher than or equal to 9.9.

18. The process according to claim 14, wherein the phenol compound represents from 0.2 to 8% by weight based on the total weight of the reaction medium.

19. The process according to claim 14, wherein the phenol compound/catalyst molar ratio is lower than or equal to 1000.

20. The process according to claim 14, wherein the catalyst is a palladium catalyst.

21. The process according to claim 14, wherein the process generates reaction products comprising the head-to-head dimerization of myrcene, the head-to-head dimerization of myrcene being at least 50% by weight of the reaction products.

22. The process according claim 14, further comprising a hydrogenation step, whereby hydrogenated dimers are obtained.

23. The process according to claim 14, wherein the catalyst is formed from a palladium precursor selected from [Pd(allyl)Cl]$_2$, Pd(cod)Cl$_2$, Pd2(dba)$_3$, Pd(dba)$_2$, Pd(dba), Pd(acac)$_2$, or an equimolar mixture of Pd(dba)$_3$ and Pd$_2$(dba)$_3$.

* * * * *